(12) United States Patent
Tsuchida (10) Patent No.: US 9,885,617 B2
(45) Date of Patent: Feb. 6, 2018

(54) CONTACT TYPE INTERNAL THERMOMETER

(71) Applicant: CITIZEN HOLDINGS CO., LTD., Tokyo (JP)

(72) Inventor: Masato Tsuchida, Sayama (JP)

(73) Assignee: CITIZEN WATCH CO., LTD., Tokyo (JP)

( * ) Notice: Subject to any disclaimer, the term of this patent is extended or adjusted under 35 U.S.C. 154(b) by 706 days.

(21) Appl. No.: 14/389,382

(22) PCT Filed: Feb. 21, 2013

(86) PCT No.: PCT/JP2013/054378
§ 371 (c)(1),
(2) Date: Sep. 30, 2014

(87) PCT Pub. No.: WO2013/145969
PCT Pub. Date: Oct. 3, 2013

(65) Prior Publication Data
US 2015/0055681 A1    Feb. 26, 2015

(30) Foreign Application Priority Data

Mar. 30, 2012 (JP) ................... 2012-081614

(51) Int. Cl.
*G01K 7/42* (2006.01)
*G01K 1/16* (2006.01)
(Continued)

(52) U.S. Cl.
CPC .............. *G01K 7/16* (2013.01); *G01K 1/165* (2013.01); *G01K 7/427* (2013.01); *G01K 13/002* (2013.01); *A61B 5/01* (2013.01)

(58) Field of Classification Search
CPC ...................................... G01K 1/165
See application file for complete search history.

(56) References Cited

U.S. PATENT DOCUMENTS

| 4,174,065 A | 11/1979 | Knauth |
| 4,648,055 A * | 3/1987 | Ishizaka ............ G01K 3/00 |
| | | 374/107 |

(Continued)

FOREIGN PATENT DOCUMENTS

| CN | 1380536 A | 11/2002 |
| CN | 1395478 A | 2/2003 |

(Continued)

OTHER PUBLICATIONS

Dengjin Zhou, et al, "Shanghai Measurement and Testing, Issue 4", Apr. 30, 2011, Method for Improving Reliability of Contac-Type SurfaceThermometre, pp. 46-48. Pertinent parts discussed in Partial Translation of the Office Action of Dec. 17, 2015, relating CN application No. 201380017565.4.

(Continued)

*Primary Examiner* — Clayton E LaBalle
*Assistant Examiner* — Leon W Rhodes, Jr.
(74) *Attorney, Agent, or Firm* — Hubbs, Enatsky & Inoue PLLC (57) ABSTRACT

Provided is a contact type internal thermometer including: a measurement surface that is brought into contact with a measurement object; a first temperature sensor stack including a first measurement surface side temperature sensor and a first back surface side temperature sensor arranged on opposite sides of a first thermal resistor; a second temperature sensor stack including a second measurement surface side temperature sensor and a second back surface side temperature sensor arranged on opposite sides of a second thermal resistor; and a controller configured to calculate an internal temperature of the measurement object based on measurement results of the respective temperature sensors, in which the controller has a first mode of calculating the internal temperature based on a heat conduction equation in (Continued)

a non-steady state, and a second mode of calculating the internal temperature based on a heat conduction equation in a steady state.

5 Claims, 6 Drawing Sheets

(51) Int. Cl.
*G01K 7/16* (2006.01)
*G01K 13/00* (2006.01)
*A61B 5/01* (2006.01)

(56) References Cited

U.S. PATENT DOCUMENTS

| | | | | |
|---|---|---|---|---|
| 5,392,031 | A * | 2/1995 | Toriumi | G01K 7/42 340/588 |
| 5,473,629 | A * | 12/1995 | Muramoto | G01K 13/002 374/102 |
| 5,738,441 | A * | 4/1998 | Cambridge | G01K 7/42 374/102 |
| 6,280,397 | B1 * | 8/2001 | Yarden | G01K 13/002 374/E13.002 |
| 6,383,144 | B1 | 5/2002 | Mooney et al. | |
| 7,597,668 | B2 * | 10/2009 | Yarden | G01K 1/165 374/102 |
| 2002/0128568 | A1 | 9/2002 | Mooney et al. | |
| 2002/0150143 | A1 | 10/2002 | Tokita et al. | |
| 2002/0191675 | A1 | 12/2002 | Tokita et al. | |
| 2005/0163190 | A1 | 7/2005 | Tokita et al. | |
| 2005/0220170 | A1 | 10/2005 | Tokita et al. | |
| 2007/0274370 | A1 | 11/2007 | Niiyama et al. | |
| 2008/0045855 | A1 | 2/2008 | Mooney et al. | |
| 2008/0294065 | A1 * | 11/2008 | Waldhoff | A61B 5/01 600/549 |
| 2009/0022202 | A1 * | 1/2009 | Yamamoto | G01K 13/002 374/104 |
| 2009/0171175 | A1 * | 7/2009 | Li | A61B 5/14551 600/324 |
| 2011/0021891 | A1 * | 1/2011 | Yokoyama | A61B 5/026 600/316 |
| 2011/0243183 | A1 | 10/2011 | Goto | |
| 2012/0083710 | A1 * | 4/2012 | Yarden | A61B 5/6802 600/549 |
| 2014/0036956 | A1 | 2/2014 | Goto | |
| 2014/0278201 | A1 * | 9/2014 | Shimizu | G01K 13/002 702/131 |

FOREIGN PATENT DOCUMENTS

| | | |
|---|---|---|
| CN | 101074893 A | 11/2007 |
| JP | 2004-177346 A | 6/2004 |
| JP | 3863192 B2 | 12/2006 |
| JP | 2008-076144 A | 4/2008 |
| JP | 2009-222543 A | 10/2009 |
| JP | 2009-236624 A | 10/2009 |
| JP | 2009236624 A * | 10/2009 |
| JP | 4600170 B2 | 12/2010 |
| JP | 2011-185819 | 9/2011 |
| JP | 2011-215107 A | 10/2011 |
| WO | 98/50766 A1 | 11/1998 |

OTHER PUBLICATIONS

Partial Translation of Office Action of Dec. 17, 2015, relating CN application No. 201380017565.4.

The partial translation of OA for corresponding Cinese Patent Application No. 201380017368.2. dated Dec. 9, 2015.

The partial translation of OA for relating Patent Application No. JP2012-081616 dated Sep. 29, 2015.

* cited by examiner

CONTACT TYPE INTERNAL THERMOMETER

CROSS REFERENCE TO RELATED APPLICATIONS

This application is a National Stage of International Application No. PCT/JP2013/054378 filed Feb. 21, 2013, claiming priority based on Japanese Patent Application No. 2012-081614 filed on Mar. 30, 2012. The contents of each of the above documents are incorporated herein by reference in their entirety.

TECHNICAL FIELD

The present invention relates to a contact type internal thermometer.

BACKGROUND ART

In various situations, there are demands for rapid, accurate, and convenient (that is, non-invasive) measurement of an internal temperature instead of a surface temperature of an object to be measured (hereinafter referred to as "measurement object"). Measurement of temperatures of biological bodies, including a human body, is a typical example of those demands. However, it is generally difficult to measure the internal temperature (sometimes referred to as deep/core body temperature, etc.) of the internal region of the biological body, that is, the temperature of the biological body in an internal region that is considered to be held substantially at a constant temperature due to blood flow. When the measurement object is a human body, holding a thermometer at a position where heat is not easily lost, such as under the tongue or arm, reading the thermometer after a thermal equilibrium state is attained between the thermometer and the human body, and then adopting the temperature read as the body temperature, is the common way often used. However, it takes a long time of about 5 minutes to 10 minutes to attain the thermal equilibrium state, and the obtained body temperature does not always match with the internal temperature of the human body. Therefore, it may be difficult to apply such a method to an object having difficulty in undergoing long-term body temperature measurement, such as babies and patients with a certain injury or disease. Further, it is difficult to obtain a body temperature with accuracy high enough for precise body temperature management.

In view of the above, as a thermometer for rapidly and accurately measuring the internal temperature of the human body, there has been proposed a thermometer configured to use a set of sensors including a first temperature sensor that is brought into contact with the body surface and a second temperature sensor arranged so as to oppose the first temperature sensor across a heat insulating member, to thereby obtain the internal temperature based on the temperature measurement results of the respective temperature sensors.

For example, in JP 3863192 B, there is described a high speed accurate temperature measuring device configured to use one set of sensors to mathematically solve a heat conduction equation in a non-steady state, to thereby estimate the internal temperature of the measurement object.

Further, in JP 4600170 B, there is disclosed a thermometer configured to use two sets of sensors, in which a heat insulating member is further arranged between the second temperature sensor (intermediate sensor) and outside air. In this manner, values of the heat fluxes passing through respective sensor sets are caused to differ. In the thermometer of the same patent literature, the internal temperature of the measurement object is calculated based on the output of each sensor in a steady state.

SUMMARY OF INVENTION

Technical Problem

In the case of the method of estimating the internal temperature in the non-steady state with use of the one set of sensors as in Patent Literature 1, the internal temperature can be reliably measured in a short period of time, but when successive measurement is attempted in a situation where the temperature of the set of sensors is sufficiently increased, such as immediately after the measurement is performed once, the set of sensors may reach the steady state to interrupt the measurement. In such a case, it is required to wait for a long time for a sufficient decrease in temperature of the set of sensors through natural heat dissipation.

On the other hand, in the case of the method of calculating the internal temperature in the steady state as in Patent Literature 2, there is no specific problem in successive measurement, but in the first measurement (such as when the thermometer is at room temperature), it takes a substantial amount of time until the sets of sensors reach the steady state, and hence fast measurement is difficult.

The present invention has been made in view of the above-mentioned circumferences, and has an object to enable fast and successive measurement in a contact type internal thermometer.

Note that the description so far mainly concerns a thermometer for measuring the internal temperature of the human body as a typical example of the contact type internal thermometer. However, the contact type internal thermometer according to the present invention is not limited thereto, and is applicable to any measurement object that requires measurement of its internal temperature in a non-invasive manner, regardless of whether it is living or non-living matter.

Solution to Problem

In order to achieve the above-mentioned object, the invention disclosed in this application has various aspects, and typical aspects are summarized in the following.

(1) A contact type internal thermometer includes at least: a measurement surface that is brought into contact with a surface to be measured of a measurement object so as to calculate an internal temperature of the measurement object; a first temperature sensor stack including a first measurement surface side temperature sensor arranged on a measurement surface side of a first thermal resistor, and a first back surface side temperature sensor arranged on a back surface side of the first thermal resistor; a second temperature sensor stack including a second measurement surface side temperature sensor arranged on a measurement surface side of a second thermal resistor, and a second back surface side temperature sensor arranged on a back surface side of the second thermal resistor; and a controller configured to calculate the internal temperature of the measurement object based on measurement results of the first measurement surface side temperature sensor, the first back surface side temperature sensor, the second measurement surface side temperature sensor, and the second back surface side temperature sensor, in which the controller has a first mode of calculating the internal temperature based on a heat conduction equation in a non-steady state, and a second mode of calculating the internal temperature based on a heat conduction equation in a steady state.

(2) In the contact type internal thermometer according to the aspect (1), the controller detects the steady state and the non-steady state to switch between the first mode and the second mode.

(3) In the contact type internal thermometer according to the aspect (2), the controller detects the non-steady state based on temporal changes of temperature measurement values of the first measurement surface side temperature sensor and the first back surface side temperature sensor when the first temperature sensor stack and the second temperature sensor stack are thermally in the non-steady state.

(4) In the contact type internal thermometer according to the aspect (3), the controller detects the steady state based on a fact that the first temperature sensor stack and the second temperature sensor stack have thermally reached the steady state during measurement of the temporal changes of the temperature measurement values of the first measurement surface side temperature sensor and the first back surface side temperature sensor.

(5) The contact type internal thermometer according to any one of the aspects (1) to (4) further includes a ventilation mechanism configured to ventilate a space in which the first temperature sensor stack and the second temperature sensor stack are arranged after the internal temperature is calculated by the controller.

Advantageous Effects of Invention

According to the above-mentioned aspect (1) or (2), in the contact type internal thermometer, fast and successive measurement is possible.

According to the above-mentioned aspect (2), the internal temperature can be rapidly calculated when the temperature sensor stack is in the non-steady state.

According to the above-mentioned aspect (3), even when the temperature sensor stack reaches the steady state during measurement in the non-steady state, the internal temperature can be accurately calculated based on the heat conduction equation in the steady state.

According to the above-mentioned aspect (4), it is possible to measure the internal temperature of the measurement object accurately during the successive measurement.

DESCRIPTION OF EMBODIMENT

Now, an embodiment of the present invention is described in detail with reference to the drawings.

Figure 1:
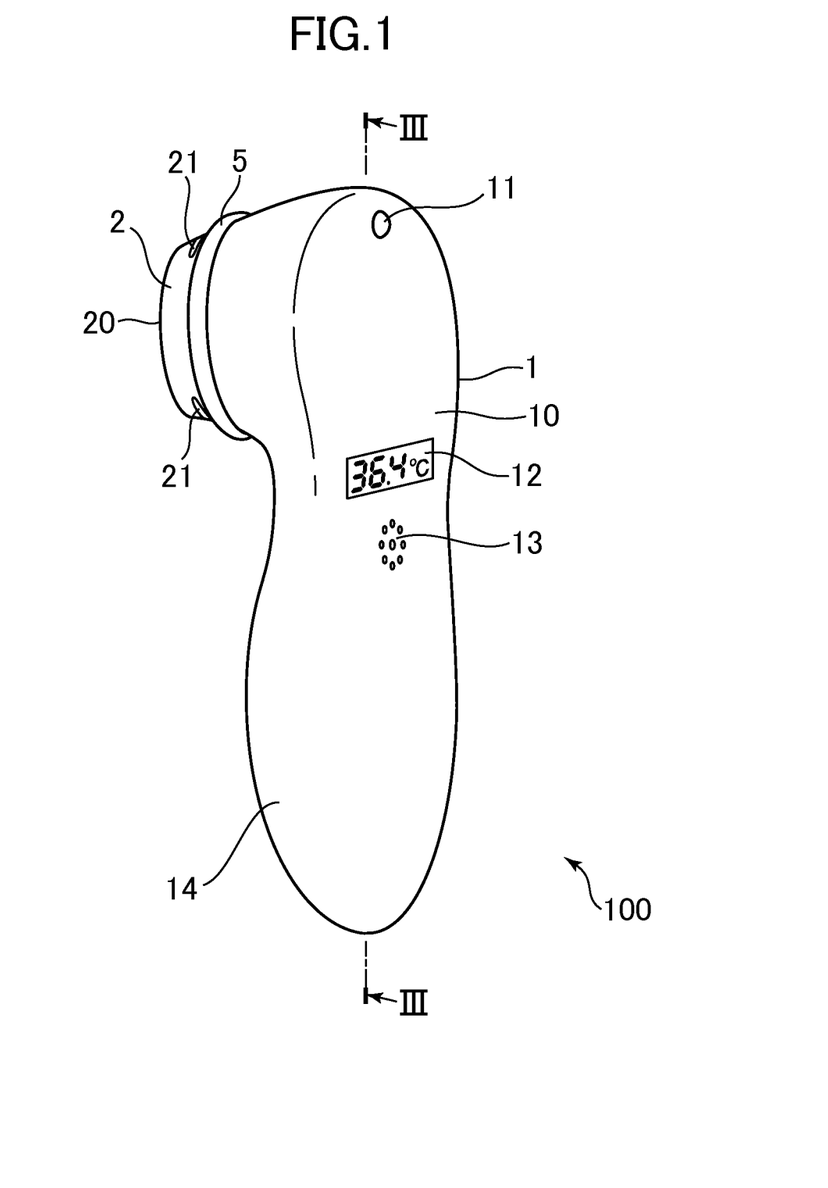
FIG. 1 is an external view of a contact type internal thermometer according to an embodiment of the present invention as viewed from a back surface side thereof.
Figure 2:
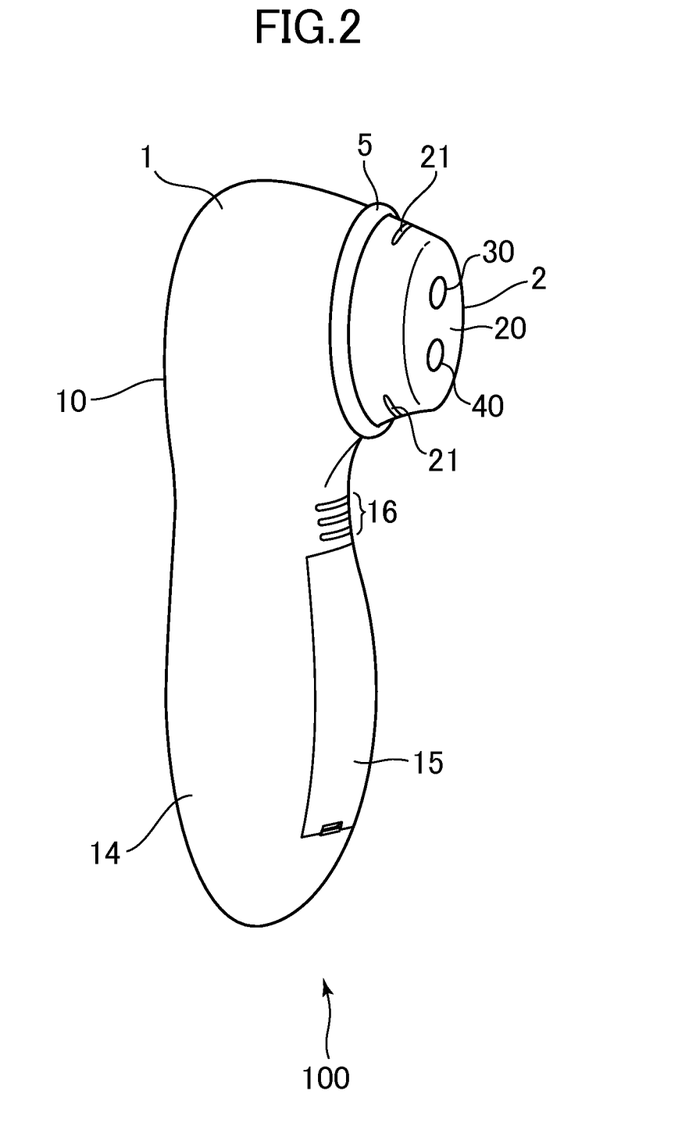
FIG. 2 is an external view of the contact type internal thermometer according to the embodiment of the present invention as viewed from a measurement surface side thereof.

FIG. 1 is an external view of a contact type internal thermometer 100 according to the embodiment of the present invention as viewed from a back surface side thereof, and FIG. 2 is an external view of the contact type internal thermometer 100 according to the same embodiment as viewed from a measurement surface side thereof. Note that in this specification, the contact type internal thermometer means a thermometer that is brought into contact with a surface of a measurement object to measure an internal temperature thereof. Further, the internal temperature means not a surface temperature of the measurement object, but a temperature of a part inside the measurement object, which is substantially considered as a constant-temperature heat source. Note that "substantially considered as a constant-temperature heat source" means that, in a case where the heat capacity inside the measurement object is large, or as a result of constant supply of heat inside the measurement object, it is considered that measurement by the contact type internal thermometer does not affect the temperature in practical use. For example, when the measurement object is a biological body, heat is constantly supplied from the trunk due to blood flow, which corresponds to the latter case.

The contact type internal thermometer 100 described in this embodiment is a portable type thermometer as illustrated in the drawings, and has a measurement head 2 mounted on a leading end of a case 1. The measurement head 2 is provided so as to protrude from the case 1, and the leading end thereof is formed into a substantially flat measurement surface 20. The measurement surface 20 is brought into contact with a surface to be measured of the measurement object, for example, the skin, to thereby measure its internal temperature. On the measurement surface 20, as illustrated in FIG. 2, a first probe 30 and a second probe 40 each having a substantially circular shape are arranged in series along the longitudinal direction of the contact type internal thermometer 100. Note that arrangement of those first probe 30 and second probe 40 is arbitrary, and the arrangement direction need not necessarily be the longitudinal direction of the contact type internal thermometer 100.

In a back surface 10 of the case 1, which is a surface on the opposite side to the measurement surface 20, a lamp 11, a display 12, and a buzzer 13 are provided. In this specification, a direction in which the measurement surface 20 is directed is hereinafter referred to as a measurement surface side, and a direction in which the back surface is directed, which is opposite to the measurement surface side, is hereinafter referred to as a back surface side. Further, the case 1 has a long and rounded shape, and has a grip 14 to be held by a user. As seen in FIG. 2, a battery case lid 15 is provided on the measurement surface side of the grip 14 of the case 1, and a battery can be accommodated therein as a power source for the contact type internal thermometer 100. Further, an intake hole 16 is formed at an appropriate position of the case 1, which corresponds to the position illustrated in FIG. 2 in this case, and an exhaust hole 21 is formed through a side surface of the measurement head 2. Thus, internal spaces of the case 1 and the measurement head 2 are communicated to outside air. The case 1 and the measurement head 2 are connected to each other by a support ring 5.

Note that FIGS. 1 and 2 illustrate an example of the design of the contact type internal thermometer 100. The design may be appropriately changed in consideration of the main application, marketability, and the like. Further, the arrangement of the respective components may be arbitrarily selected within a range that does not affect the function.

Figure 3:
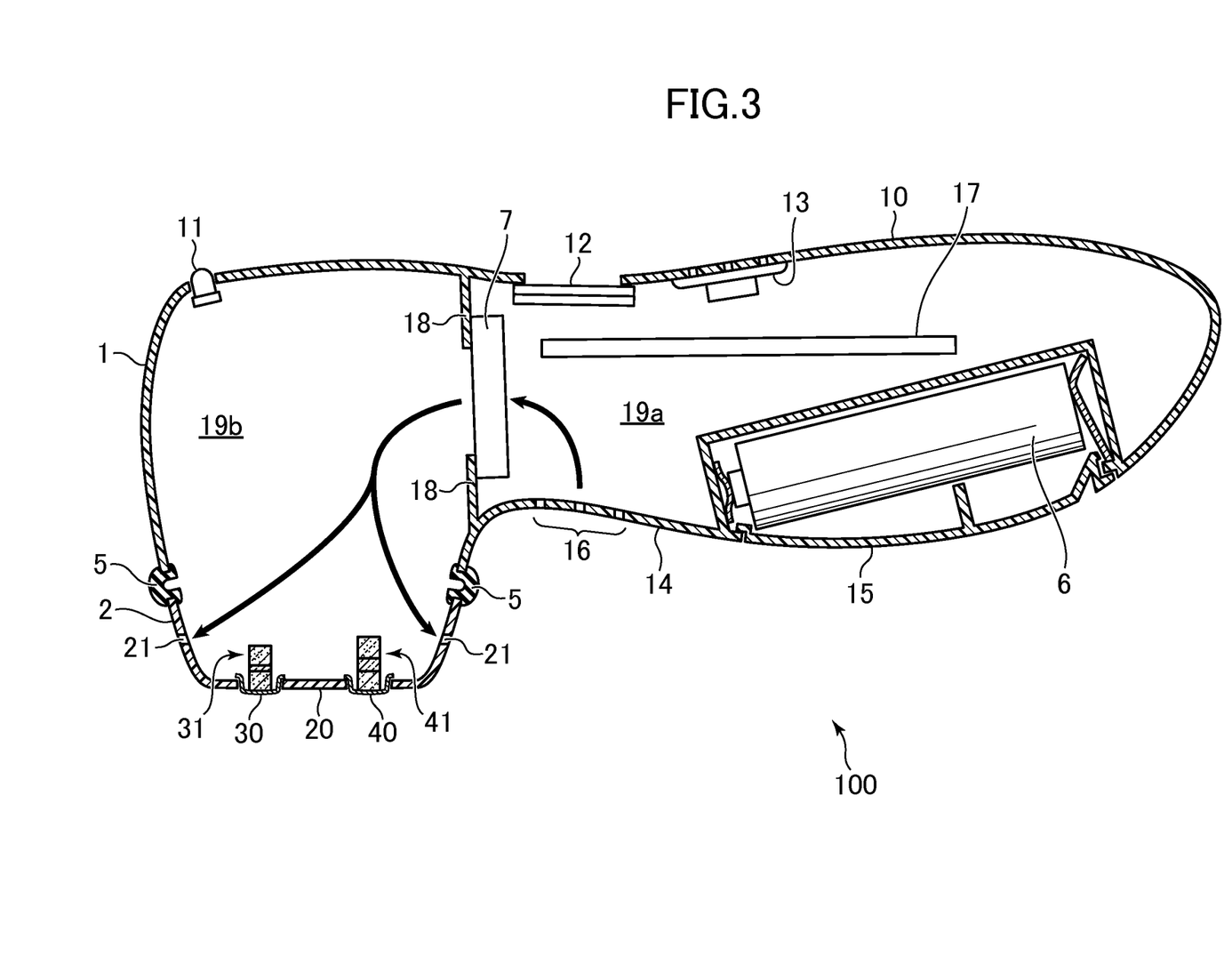
FIG. 3 is a schematic sectional view of the contact type internal thermometer taken along the line III-III of FIG. 1.

FIG. 3 is a schematic sectional view of the contact type internal thermometer 100 taken along the line III-III of FIG. 1. The case 1 is a hollow molded product made of an arbitrary synthetic resin, preferably an ABS resin, and various components of the contact type internal thermometer 100 are integrally accommodated inside the case 1. Inside the grip 14, a battery 6 and a circuit board 17 are accommodated. The circuit board 17 has various electronic components such as a controller (not shown) mounted thereon, which are supplied with power from the battery 6 so as to supply power to all components that require power and to control the operation thereof. The battery 6 illustrated in FIG. 3 is a commercially available AAA dry cell, but the form thereof may be arbitrary. The shape of the battery 6 is arbitrary, such as a button type or a square type, and also the selection of a primary cell or a secondary cell is arbitrary. Note that wiring for electrically connecting each component to the circuit board 17 is omitted in order to simplify the illustration.

The lamp 11 is preferred to be a light emitting diode capable of emitting a plurality of colors of light, and is turned on to notify the user of the state of the contact type internal thermometer 100. The display 12 is a liquid crystal display device in this embodiment, and notifies the user of the measurement result of the contact type internal thermometer 100 in a mode as illustrated in FIG. 1. As a matter of course, the display 12 may display other arbitrary information, such as a remaining amount of the battery 6. Alternatively, the display 12 may simultaneously display the state of the contact type internal thermometer 100 and the lamp 11 may be omitted. The buzzer 13 is a general electronic buzzer in this embodiment, and notifies the user of the state of the contact type internal thermometer 100 by a beep sound. Note that the type of the buzzer 13 is also arbitrary, and the buzzer 13 may be equipped with a speaker for notification by voice or a melody. Alternatively, notification may be given only by the lamp 11 and/or the display 12, and the buzzer 13 may be omitted.

Further, a partition wall 18 is provided inside the case 1, which partitions the inside of the case 1 into a grip space 19a and a head space 19b. The partition wall 18 has an opening formed therein, and a blower 7 is mounted so as to close the opening. The function of the blower 7 is described later.

The measurement head 2 is mounted on the leading end portion of the case 1 through intermediation of the support ring 5. The support ring 5 is made of a material having elasticity and excellent in heat insulating property, preferably silicon rubber or foam thereof. The support ring 5 allows a slight movement of the measurement head 2 with respect to the case 1, and blocks heat from transmitting from the measurement head 2 to the case 1. This is for reliably bringing the measurement surface 20 into close contact with the measurement object when the measurement surface 20 is brought into contact with the measurement object, and for preventing occurrence of measurement error due to outflow of heat from the measurement head 2 to the case 1. However, the support ring 5 is not always necessary. When there is no problem in close contact between the measurement surface 20 and the measurement object and when the measurement head 2 is made of a material having a sufficiently low thermal conductivity and hence has no problem in practical use, the support ring 5 may be omitted. The measurement head 2 may be directly fixed to the case 1, or the measurement head 2 and the case 1 may be integrally formed. Further, the shape of the support ring 5 is not limited to a ring shape, and a member having an arbitrary shape may be used.

The measurement head 2 is preferred to be made of a material having a stable shape, a low thermal conductivity, and a small specific heat. For example, hard urethane foam and hard vinyl chloride foam are suitably used. However, in this case also, the material is not particularly limited if there is no problem in practical use, and the material may be arbitrary.

The measurement surface 20 of the measurement head 2 has openings formed at positions corresponding to the respective first probe 30 and second probe 40, and each probe is mounted so as to protrude slightly from the measurement surface 20. Each probe is preferred to be made of a material having a high thermal conductivity, and is made of a metal in this embodiment. Note that, each probe is preferred to be made of a material having a corrosion resistance property, and aluminum and stainless steel are suitable among metal materials. Note that, as described above, the measurement head 2 itself is made of a material having a low thermal conductivity, and hence the first probe 30 and the second probe 40 are thermally separated from each other.

A first temperature sensor stack 31 is provided on the back surface side of the first probe 30, and the first temperature sensor stack 31 and the first probe 30 are thermally coupled to each other. Further, a second temperature sensor stack 41 is provided on the back surface side of the second probe 40, and the second temperature sensor stack 41 and the second probe 40 are thermally coupled to each other. The first temperature sensor stack 31 and the second temperature sensor stack 41 are described in detail later. Note that in this embodiment, two temperature sensor stacks, that is, the first temperature sensor stack 31 and the second temperature sensor stack 41, are provided, but three or more probes and three or more temperature sensor stacks may be provided for the purpose of mutual error compensation or providing backup in the case of failure.

Figure 4:
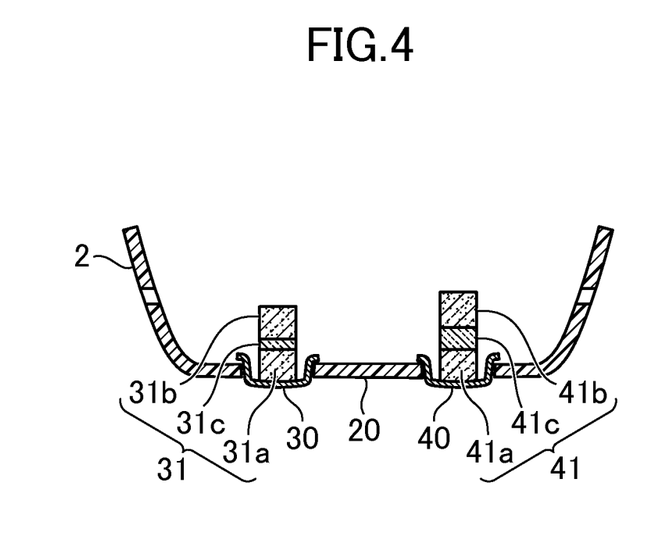
FIG. 4 is an enlarged sectional view of the vicinity of a measurement head in FIG. 3.

FIG. 4 is an enlarged sectional view of the vicinity of the measurement head 2 in FIG. 3. FIG. 4 omits the illustration of members located on the back surface side with respect to the support ring 5 of FIG. 3.

As illustrated in detail in FIG. 4, the first temperature sensor stack 31 has a structure of stacking a first measurement surface side temperature sensor 31a that is arranged on the measurement surface 20 side so as to be brought into contact and thermally coupled with the first probe 30, a first back surface side temperature sensor 31b arranged on the back surface side, and a first thermal resistor 31c arranged between the first measurement surface side temperature sensor 31a and the first back surface side temperature sensor 31b so as to function as a thermal resistor that forms a heat flow path from the first measurement surface side temperature sensor 31a to the first back surface side temperature sensor 31b. Further, the second temperature sensor stack 41 has a structure similar to that of the first temperature sensor stack 31, that is, a structure of stacking a second measurement surface side temperature sensor 41a that is arranged on the measurement surface side so as to be brought into contact and thermally coupled with the second probe 40, a second back surface side temperature sensor 41b arranged on the back surface side, and a second thermal resistor 41c arranged between the second measurement surface side temperature sensor 41a and the second back surface side temperature sensor 41b so as to function as a thermal resistor that forms a heat flow path from the second measurement surface side temperature sensor 41a to the second back surface side temperature sensor 41b. Therefore, when the measurement surface 20 is brought into contact with the measurement object, heat from the measurement object is transmitted to the first probe 30 and the second probe 40. In the first temperature sensor stack 31, the heat passes through the first measurement surface side temperature sensor 31a, the first thermal resistor 31c, and the first back surface side temperature sensor 31b in the stated order, and in the second temperature sensor stack 41, the heat passes through the second measurement surface side temperature sensor 31a, the second thermal resistor 31c, and the second back surface side temperature sensor 31b in the stated order. Then, the heat is dissipated to the atmosphere.

Any temperature sensor may be used for each temperature sensor, but a thermistor is used in this embodiment. Each temperature sensor is connected to the circuit board 17 (see FIG. 3) via wiring (not shown) so that the temperature in each temperature sensor can be detected.

Although detailed description is described later, the contact type internal thermometer 100 of this embodiment is configured to be capable of performing both of temperature measurement in the non-steady state by using one temperature sensor stack and temperature measurement in the steady state by using two temperature sensor stacks. In particular, in order to perform temperature measurement in the steady state, a difference is required between a heat flux passing through the first temperature sensor stack 31 and a heat flux passing through the second temperature sensor stack 32, and the ratio of heat resistances of the thermal resistor 31c and the thermal resistor 41c is required to be known. Therefore, as illustrated in FIG. 4, by providing a difference in thickness between the thermal resistor 31c and the thermal resistor 41c, different heat resistance values are obtained therebetween. Note that in order to achieve a difference in heat resistance value between the thermal resistor 31c and the thermal resistor 41c, a difference may be provided in geometric dimension such as a thickness as in this case, or materials thereof may be different. Alternatively, the used thermal resistor 31c and thermal resistor 41c may be the same (for example, a flexible printedboard onto which the temperature sensors are mounted), and an appropriate structure such as a radiator plate, a radiator fin, or a heat insulating member may be provided to one or both of the first back surface side temperature sensor 31b and the second back surface side temperature sensor 41b so as to adjust the heat dissipation performance. In this way, a difference may be achieved between the heat flux passing through the first temperature sensor stack 31 and the heat flux passing through the second temperature sensor stack 32.

Now, the principle of measuring the internal temperature using the contact type internal thermometer 100 of this embodiment is described. As described above, the contact type internal thermometer 100 is configured to be capable of performing both of the temperature measurement in the non-steady state by using one temperature sensor stack and the temperature measurement in the steady state by using two temperature sensor stacks, and the principle of each temperature measurement differs. Note that the operation of the controller in a state in which the contact type internal thermometer 100 measures the temperature in the non-steady state is called a first mode, and the operation of the controller in a state in which the contact type internal thermometer 100 measures the temperature in the steady state is called a second mode.

First, the measuring principle in the first mode, that is, in the non-steady state, is described. As described in Patent Literature 1, when the internal temperature as the measurement object is represented by $T_b$, the temperature at the first measurement surface side temperature sensor 31a is represented by $T_{11}$, the temperature at the first back surface side temperature sensor 31b is represented by $T_{12}$, and the temperature inside the first thermal resistor 31c at a time t is represented by T(t), the following heat conduction equation is approximately established.

$$T(t+\Delta t)-T(t)=\omega_1(T_b-T_1)-\omega_2(T_1-T_2) \quad \text{[Math. 1]}$$

There are three unknowns of $T_b$, $\omega_1$, and $\omega_2$, but because the left-hand side of Expression 1 represents temperature difference in certain time difference, values of those unknowns can be determined by measuring the temperature at least four times at different times t, with the result that the value of $T_b$ can be obtained. Note that, in the description above, the temperature is measured by using the first temperature sensor stack 31, but alternatively, the second temperature sensor stack 41 may be used.

The above is the basic principle of temperature measurement in the non-steady state. However, in order to secure the measurement accuracy, after $T_b$ is once obtained, the measurement may be continued to obtain new $T_b$. When a difference therebetween falls below a predetermined threshold, that is, when the calculation result of $T_b$ has converged, the finally obtained value may be adopted as $T_b$.

Next, the measuring principle in the second mode, that is, in the steady state is described.

Figure 5:
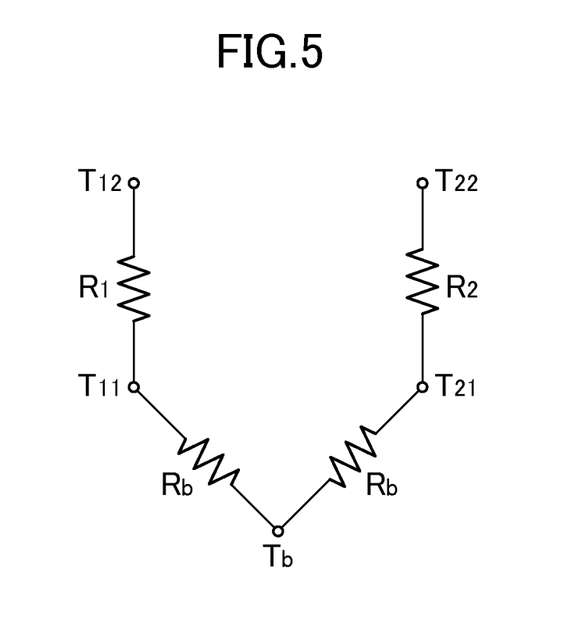
FIG. 5 is a thermal equivalent circuit diagram of a measurement section provided in the measurement head of the contact type internal thermometer according to the embodiment of the present invention.

FIG. 5 is a thermal equivalent circuit diagram of a measurement section provided in the measurement head of the contact type internal thermometer according to the embodiment of the present invention. FIG. 5 is described with reference to FIG. 4. $T_b$, $T_{11}$, and $T_{12}$ are as described above. $T_{21}$ represents a temperature of the second measurement surface side temperature sensor 41a, and $T_{22}$ represents a temperature of the second back surface side temperature sensor 41b. Further, a heat resistance $R_b$ is a heat resistance when heat transmits from the inside of the measurement object through the first probe 30 and the second probe 40 to the first measurement surface side temperature sensor 31a and the second measurement surface side temperature sensor 41a, a heat resistance $R_1$ is a heat resistance of the first thermal resistor 31c, and a heat resistance $R_2$ is a heat resistance of the second thermal resistor 41c. Further, $T_b > T_{11} > T_{12}$ and $T_b > T_{21} > T_{22}$ are satisfied.

When it is assumed that the illustrated system is in a steady state, a heat flux flowing from $T_b$ to $T_{12}$ is constant, and hence the following heat conduction equation is satisfied.

$$\frac{(T_{11} - T_{12})}{R_1} = \frac{(T_b - T_{11})}{R_b} \quad \text{[Math. 2]}$$

$$\frac{(T_{21} - T_{22})}{R_2} = \frac{(T_b - T_{21})}{R_b} \quad \text{[Math. 3]}$$

$$T_b = \frac{T_{21}(T_{11} - T_{12}) - KT_{11}(T_{21} - T_{22})}{(T_{11} - T_{12}) - K(T_{21} - T_{22})} \quad \text{[Math. 4]}$$

Note that K corresponds to $R_1/R_2$, which is obtained in advance through experiment or calculation.

The above is the basic principle of temperature measurement in the steady state.

Figure 6:
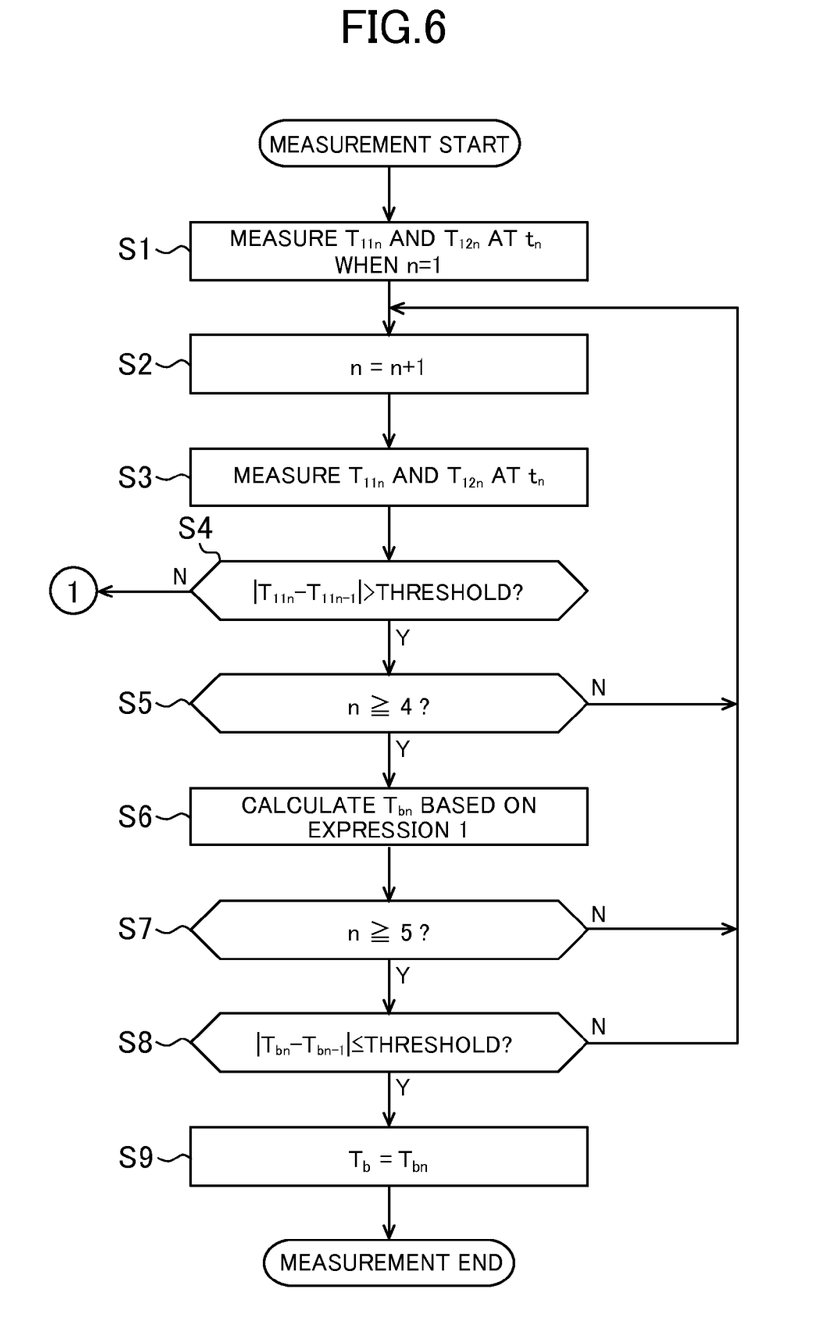
FIG. 6 is a flowchart illustrating an algorithm for measuring an internal temperature using the contact type internal thermometer according to the embodiment of the present invention.
Figure 7:
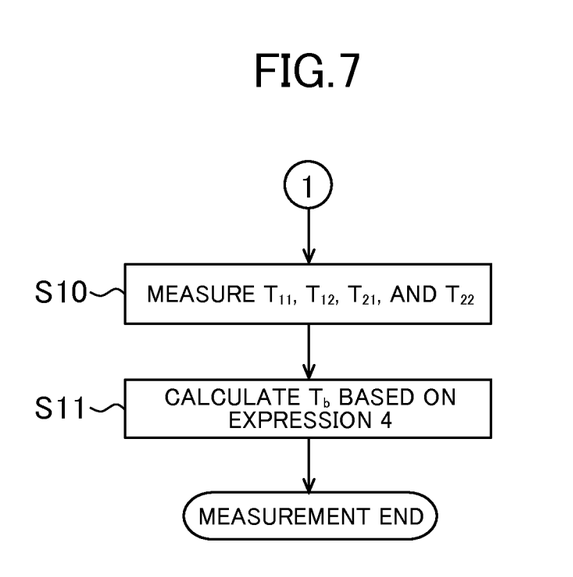
FIG. 7 is a flowchart illustrating an algorithm for measuring the internal temperature using the contact type internal thermometer according to the embodiment of the present invention.

FIGS. 6 and 7 are flowcharts illustrating an algorithm for measuring the internal temperature by the contact type internal thermometer 100 according to this embodiment. Note that the control illustrated in FIGS. 6 and 7 is performed by the controller mounted on the circuit board 17 of the contact type internal thermometer 100. The controller is an appropriate information processing device such as a microcontroller, and calculates the internal temperature $T_b$ of the measurement object based on the measurement results of the first measurement surface side temperature sensor 31a, the first back surface side temperature sensor 31b, the second measurement surface side temperature sensor 41a, and the second back surface side temperature sensor 41b.

Note that the flowchart illustrated in FIG. 6 represents control in the first mode, and the flowchart illustrated in FIG. 7 represents control in the second mode.

When the measurement is started, in Step S1, the controller first substitutes 1 into the variable n and measures $T_{11n}$ and $T_{12n}$ at time $t_n$. The subscript n of the time t represents that time has elapsed as the value becomes larger. Further, the subscript n of the temperature T represents that the temperature T is obtained at the time $t_n$.

Subsequently in Step S2, n is incremented by 1. With this, the time proceeds from $t_1$ to $t_2$. Further, in Step S3, $T_{11n}$ and $T_{12n}$ are measured again. At this time, $T_{11}$ and $T_{12}$ previously obtained in Step S1 become $T_{11n-1}$ and $T_{12n-1}$, respectively.

Then, in Step S4, it is determined whether or not the absolute value of $T_{11n}$-$T_{11n-1}$ is larger than a predetermined threshold. This determination examines the magnitude of the temperature change at $T_{11}$ when the time changes from $t_{n-1}$ to $t_n$. When the magnitude of this temperature change is larger than a predetermined value, the first temperature sensor stack 31 is thermally in the non-steady state, and otherwise the first temperature sensor stack 31 is thermally in the steady state. Note that this determination is performed only by referring to $T_{11}$ in this example, but any other values that can be obtained, such as $T_{12}$, $T_{21}$, and $T_{22}$, may be used. Alternatively, determination may be performed for all of those values, or an average or a sum of those values may be used.

When the result of Step S4 is YES, that is, in the case of the non-steady state, in subsequent Step S5, whether or not the temperature measurement has been performed for a given number of times, that is, 4 times or more, is determined based on the value of n. When the number of times of temperature measurement has not reached 4, $T_b$ cannot be obtained based on Expression 1, and hence the processing returns to Step S2.

When the temperature measurement has been performed for the given number of times or more, the processing proceeds to Step S6, and $T_{bn}$ is obtained based on Expression 1. Note that in this case, $T_{bn}$ is obtained based on the measurement result in the first temperature sensor stack 31, but alternatively, $T_{bn}$ may be obtained based on the measurement result in the second temperature sensor stack 41.

Subsequently in Step S7, whether or not $T_{bn}$ is obtained twice or more is determined based on the value of n. This is because it is necessary to obtain $T_{bn}$ at least twice in order to determine the presence or absence of convergence of $T_{bn}$ in next Step S8. When $T_{bn}$ is not obtained twice or more, the processing returns to Step S2.

In Step S8, it is determined whether the absolute value of $T_{bn}$-$T_{bn-1}$ is equal to or smaller than a predetermined threshold. This determination examines the magnitude of the change of $T_{bn}$ when the time changes from $t_{n-1}$ to $t_n$. When the magnitude of this change is equal to or smaller than a predetermined value, it is considered that $T_{bn}$ has converged and thus correct $T_b$ is obtained. When $T_{bn}$ has not converged, the processing returns to Step S2, and when $T_{bn}$ has converged, $T_{bn}$ is adopted as $T_b$ in Step S9, and the measurement is ended.

In the above-mentioned flow, in Steps S5 and S7, while the temperature measurement is repeated until reaching the given number of times, as illustrated in Step S4, it is determined whether or not the temperature sensor stack is in the steady state, and when the temperature sensor stack is in the steady state, transfer is made to control of performing the temperature measurement in the steady state as illustrated in FIG. 7. Further, in Step S8, also while the temperature measurement is repeated until the value of $T_{bn}$ calculated based on Expression 1 converges, as illustrated in Step S4, it is determined whether or not the temperature sensor stack is in the steady state, and when the temperature sensor stack is in the steady state, transfer is made to control of performing the temperature measurement in the steady state as illustrated in FIG. 7.

When the temperature sensor stack, in this case, the first temperature sensor stack 31, reaches the steady state, the processing proceeds from Step S4 to Step S10 of FIG. 7, and all of $T_{11}$, $T_{12}$, $T_{21}$, and $T_{22}$ are measured to calculate $T_b$ based on Expression 4 in Step S11. Then, the measurement is ended.

☐Subsequently, the procedure of measuring the internal temperature by using the contact type internal thermometer 100 according to this embodiment, that is, the procedure of the temperature measurement operation, is described with reference to FIGS. 1 to 4.

Procedure 1: the measurement surface 20 of the contact type internal thermometer 100 is brought into contact with the measurement object.

Procedure 2: the temperature measurement operation is started by the controller mounted on the circuit board 17. Note that the temperature measurement operation may be automatically started by detecting increase of the temperature to be measured by the first measurement surface side temperature sensor 31a or the second measurement surface side temperature sensor 41a, or may be started in response to the user's operation of a switch such as a push button (not shown). At this time, the controller notifies the user of the start of the measurement by a beep sound from the buzzer 13. Simultaneously, the lamp 11 is turned on in an arbitrary color, for example, red, so as to urge the user to maintain the measurement surface 20 in a contact state with the measurement object.

Procedure 3: the controller calculates the internal temperature $T_b$ of the measurement object in accordance with the algorithm illustrated in FIGS. 6 and 7, and causes the display 12 to display the internal temperature $T_b$ as illustrated in FIG. 1. Further, by generating the beep sound using the buzzer 13, and turning on the lamp 11 in an arbitrary color different from the previous color, for example, green, the user is notified of the end of the measurement. Note that the user is notified of the calculated internal temperature $T_b$ through display on the display 12 in this embodiment, but the present invention is not limited thereto. The results may be accumulated in a memory of the contact type internal thermometer 100, or may be output through wired or wireless connection to an external device of the contact type internal thermometer 100. In this case, the display 12 is not always necessary. Further, when the calculated internal temperature $T_b$ is displayed, whether the internal temperature $T_b$ is obtained through measurement in the non-steady state or through measurement in the steady state may be displayed.

Note that, in the description above, various notifications of measurement start and measurement end are given to the user through the beep sound from buzzer 13 and the turning-on of the lamp 11, but notification methods therefor are not limited to those exemplified above. In particular, the beep sound may be omitted, or may be turned off in response to the setting by the user. It may be preferred to give various notifications to the user through only the turning-on of the lamp 11 without using the sound, such as when the measurement object is a sleeping infant because measurement can be established without interrupting the sleep of the infant. As a matter of course, how to turn on the lamp 11, for example, the selection of the emission color, is arbitrary. Further, independently of the emission color, the lamp 11 may be caused to flash, the intensity of the emitted light may be changed, or a plurality of lamps 11 may be provided to change the number or position of the turned-on lamps, to thereby give various notifications to the user. Further, as described above, various notifications may be given to the user not by the lamp 11 but by the display 12.

Procedure 4: the controller activates the blower 7 to ventilate the head space 19b. This operation is performed so as to prevent a situation where the measurement accuracy is reduced or the measurement is impossible for the following reason. That is, when the head space 19b is isolated from the outside air, along with the measurement, the heat that has passed through the first temperature sensor stack 31 and the second temperature sensor stack 41 and has been transmitted to air inside the head space 19b causes the temperature inside the head space 19b to increase, to thereby decrease the magnitudes of the heat fluxes passing through the first temperature sensor stack 31 and the second temperature sensor stack 41.

In this embodiment, the blower 7 generates an air flow that flows from the grip space 19a toward the head space 19b of FIG. 1. Therefore, as indicated by the arrow in FIG. 3, the air flow is induced by the blower 7 to be taken in through the intake hole 16, pass through the blower 7, pass the vicinity of the first temperature sensor stack 31, and be exhausted through the exhaust hole 21. Therefore, the blower 7, the intake hole 16, and the exhaust hole 21 of this embodiment cooperate with each other to constitute a ventilation mechanism for ventilating the head space 19b.

Note that the configuration of the ventilation mechanism is arbitrary, and the arrangement of the blower 7, the intake hole 16, and the exhaust hole 21 is also arbitrary. Further, the intake and exhaust directions may be reversed. Further, the form of the blower 7 is not particularly limited, and may be a general fan or a micro-blower using a piezoelectric element. Alternatively, if there is no problem in the ventilation performance, the blower 7 may be omitted, and the ventilation mechanism may be constructed of only the intake hole 16 and the exhaust hole 21.

According to the contact type internal thermometer 100 described above, while the temperature sensor stack is in the non-steady state, the internal temperature of the measurement object is calculated based on the heat conduction equation in the non-steady state. In contrast, when the temperature sensor stack is in the steady state, the internal temperature of the measurement object is calculated based on the heat conduction equation in the steady state. Therefore, fast and successive measurement is possible.

The specific configurations in the embodiment above are described as an example, and the invention disclosed in this specification is not limited to those specific configurations themselves. Various modifications may be made to the disclosed embodiment by a person skilled in the art. For example, the shape, number, and arrangement of each member or a part thereof may be appropriately changed, and it is intended that the technical scope of the invention disclosed in this specification cover all such modifications.

The invention claimed is:

1. A contact type internal thermometer, comprising:
   a measurement surface that is brought into contact with a surface to be measured of a measurement object so as to calculate an internal temperature of the measurement object;
   a first temperature sensor stack comprising a first measurement surface side temperature sensor arranged on a measurement surface side of a first thermal resistor, and a first back surface side temperature sensor arranged on a back surface side of the first thermal resistor;
   a second temperature sensor stack comprising a second measurement surface side temperature sensor arranged on a measurement surface side of a second thermal resistor, and a second back surface side temperature sensor arranged on a back surface side of the second thermal resistor; and
   a controller configured to calculate the internal temperature of the measurement object based on measurement results of the first measurement surface side temperature sensor, the first back surface side temperature sensor, the second measurement surface side temperature sensor, and the second back surface side temperature sensor,
   wherein the controller has a first mode of calculating the internal temperature based on a heat conduction equation in a non-steady state, and a second mode of calculating the internal temperature based on a heat conduction equation in a steady state,
   wherein a heat flux in the steady state is constant,
   wherein the controller detects the steady state and the non-steady state to switch between the first mode and the second mode.

2. The contact type internal thermometer according to claim 1, wherein the controller detects the non-steady state based on temporal changes of temperature measurement values of the first measurement surface side temperature sensor and the first back surface side temperature sensor when the first temperature sensor stack and the second temperature sensor stack are thermally in the non-steady state.

3. The contact type internal thermometer according to claim 2, wherein the controller detects the steady state when the first temperature sensor stack and the second temperature sensor stack have reached the thermal steady state during measurement of the temporal changes of the temperature measurement values of the first measurement surface side temperature sensor and the first back surface side temperature sensor.

4. The contact type internal thermometer according to claim 1, further comprising a ventilation mechanism configured to ventilate a space in which the first temperature sensor stack and the second temperature sensor stack are arranged, after the internal temperature is calculated by the controller.

5. The contact type, internal thermometer according to claim 4, wherein the ventilation mechanism comprises:
   a blower;
   an intake port; and
   an exhaust port;

wherein the blower, intake port and exhaust port are all formed in cooperation with each other.

* * * * *